United States Patent

Campbell et al.

[11] Patent Number: 6,031,144
[45] Date of Patent: *Feb. 29, 2000

[54] PROCESS FOR REDUCING THE RESIDUAL OLEFIN CONTENT OF AN ALKYLATION REACTION PRODUCT

[75] Inventors: Curt B. Campbell, Hercules; Thomas V. Harris, Benicia, both of Calif.

[73] Assignee: Chevron Chemical Company LLC, San Francisco, Calif.

[*] Notice: This patent is subject to a terminal disclaimer.

[21] Appl. No.: 08/906,951

[22] Filed: Aug. 6, 1997

[51] Int. Cl.⁷ ............................................. C07C 2/64
[52] U.S. Cl. ........................... 585/449; 585/323; 585/470
[58] Field of Search ................................. 585/323, 449, 585/470; 208/64, 134

[56] References Cited

U.S. PATENT DOCUMENTS

| | | | |
|---|---|---|---|
| 4,503,277 | 3/1985 | Himes | 585/455 |
| 4,795,550 | 1/1989 | Sachtler et al. | 208/307 |
| 5,300,722 | 4/1994 | Steigelmann et al. | 585/467 |
| 5,705,724 | 1/1998 | Collins et al. | 585/446 |
| 5,847,251 | 12/1998 | Sy | 585/323 |
| 5,866,736 | 2/1999 | Chen | 585/323 |

FOREIGN PATENT DOCUMENTS

| | | |
|---|---|---|
| 1034962 | 7/1978 | Canada . |
| WO97/47573 | 12/1997 | WIPO . |

*Primary Examiner*—Walter D. Griffin
*Assistant Examiner*—Tam M. Nguyen
*Attorney, Agent, or Firm*—Steven G.K. Lee; Ernest A. Schaal

[57] ABSTRACT

The residual olefin content of the alkylation reaction product of a single-ring aromatic hydrocarbon with an olefin is reduced by removing at least a portion of the non-alkylated single-ring aromatic hydrocarbon, then reacting the remaining alkylation reaction product at about atmospheric pressure and at a temperature of about from 100° to 250° C. in the presence of an acidic catalyst. The olefin has at least sixteen carbon atoms. The acidic catalyst can be a molecular sieve (such as a natural or synthetic zeolite) or clay.

8 Claims, No Drawings

PROCESS FOR REDUCING THE RESIDUAL OLEFIN CONTENT OF AN ALKYLATION REACTION PRODUCT

The present invention relates to a process for reducing the residual olefin content of the alkylation reaction product of a single-ring aromatic hydrocarbon (such as toluene) with an olefin having at least sixteen carbon atoms.

BACKGROUND OF THE INVENTION

The alkylation of aromatics with a variety of Lewis or Brönsted acid catalysts is well known. Typical commercial catalysts include phosphoric acid/kieselguhr, aluminum chloride, and hydrogen fluoride. Alkylation with lower molecular weight olefins, such as propylene, can be carried out in the liquid or vapor phase. For alkylations with higher olefins, such as $C_{16+}$ olefins, the alkylations are done in the liquid phase, usually in the presence of hydrogen fluoride. Alkylations of benzene with higher olefins is especially difficult, and requires hydrogen fluoride treatment. Such a process is disclosed by Himes in U.S. Pat. No. 4,503,277, entitled "HF Regeneration in Aromatic Hydrocarbon Alkylation Process," which is hereby incorporated by reference in its entirety for all purposes.

It has been found that in some cases, in the alkylation of aromatics with long chain olefins, conversion is insufficient to remove the last traces of olefins. When excess aromatic is stripped from the product, the residual high boiling long chain olefins are not distilled out. This residual olefin can lead to poor product properties.

U.S. Pat. No. 4,795,550 discloses a process for reducing the residual olefin content from hydrocarbon process streams containing substantially aromatic and napthenic hydrocarbons having from 6 to 20 carbon atoms per molecule. This process occurs at reaction conditions which ensure liquid phase operation with a solid catalyst, preferably zeolite Y, in a fixed bed reactor operating at a liquid hourly space velocity of 1 to 10 $hour^{-1}$ by a catalytic olefin-consuming alkylation reaction to produce an essentially olefin-free product. The essentially olefin-free product has approximately the same quantity and distribution of aromatic and napthenic hydrocarbons as contained in the original process stream. U.S. Pat. No. 4,795,550 is hereby incorporated by reference in its entirety for all purposes.

SUMMARY OF THE INVENTION

The present invention provides a process for reducing the residual olefin content of the alkylation reaction product of a single-ring aromatic hydrocarbon with an olefin having at least sixteen carbon atoms. That process comprises first removing at least some of the non-alkylated single-ring aromatic hydrocarbon from the alkylation reaction product; then reacting the remaining alkylation reaction product at a pressure of about from 0 to 1 bar, preferably at atmospheric pressure, and at a temperature of about from 100° to 250° C. in the presence of an acidic catalyst. The acidic catalyst can be a molecular sieve or clay. Preferably, the molecular sieve is a natural zeolite or a synthetic zeolite.

Unlike U.S. Pat. No. 4,795,550, which reduces the residual olefin content without changing the quantity and distribution of aromatic and napthenic hydrocarbons, our process produces a product containing an increased amount of heavy alkylate. That heavy alkylate can be advantageous to the product.

Preferably, the single-ring aromatic hydrocarbon is benzene, toluene, xylene, or a mixture thereof. Most preferably, it is toluene.

The olefin, with which the single-ring aromatic hydrocarbon is reacted, has at least 16 carbon atoms. Preferably, it has from 20 to 28 carbon atoms. More preferably, it has from 20 to 24 carbon atoms.

DETAILED DESCRIPTION OF THE INVENTION

In its broadest aspect, the present invention involves a process for reducing the residual olefin content of the alkylation reaction product of a single-ring aromatic hydrocarbon with an olefin having at least sixteen carbon atoms.

That process comprises two steps. In the first step, at least a portion of the non-alkylated single-ring aromatic hydrocarbon is removed from the alkylation reaction product. In the second step, the product of the first step is reacted at a pressure of about from 0 to 1 bar (preferably at atmospheric pressure) and at a temperature of about from 100° to 250° C. in the presence of an acidic catalyst.

Since the process of the present invention reduces the residual olefin content of the alkylation reaction product, it can be referred to as a "reduced olefin content process." By "residual olefin content," we mean the unreacted olefin remaining after an alkylation of an aromatic hydrocarbon.

ALKYLATION REACTION PRODUCT

By the phrase "alkylation reaction product," we mean the reaction product of the alkylation of a single-ring aromatic hydrocarbon with a long olefin (at least 16 carbon atoms). The alkylation reaction product is the feed for the process of the present invention.

The single-ring aromatic hydrocarbon that is alkylated can be benzene, toluene, ethylbenzene, cumene, xylene, or mixtures thereof. Preferably, the single-ring aromatic hydrocarbon is benzene, toluene, xylene, or mixtures thereof. More preferably, it is toluene.

Preferably, the olefin is a mixture of normal alpha olefins, but the olefins can be isomerized and/or contain some degree of branching. Preferably, the olefins have from 20 to 28 carbon atoms. More preferably, they have from 20 to 24 carbon atoms.

The alkylation reaction product can be formed by any conventional process, such as processes similar to those disclosed by Resh in U.S. Pat. No. 4,691,098 entitled "Process for Production of Alkyl Aromatics," and those disclosed by Kocal in U.S. Pat. No. 5,334,793 entitled "Increasing Catalyst Life and Improving Product Linearity in the Alkylation of Aromatics with Linear Olefins." Both U.S. Pat. Nos. 4,691,098 and 5,334,793 are hereby incorporated by reference in their entirety for all purposes.

The alkylation reaction product typically comprises up to five weight percent residual olefin content and up to two weight percent non-alkylated single-ring aromatic hydrocarbon. By "non-alkylated single-ring aromatic hydrocarbon," we mean the single-ring aromatic hydrocarbon remaining unreacted after alkylation.

Preferably, the mono-alkylate content of alkylation reaction product is at least 80 weight percent. By "mono-alkylate content," we mean the amount of single-ring aromatic hydrocarbon that has one long-chain alkyl group attached to the aromatic ring. The remainder typically comprises minor amounts of unreacted materials and heavy alkylate. By "heavy alkylate", we mean the amount of total alkylate that is comprised of those chemical species present with molecular weights higher than that of the mono-alkylate. These chemical species present with molecular weights higher than that of the mono-alkylate may be composed of, but are not limited to:

(a) mono-alkylated aromatics of oligomerized olefins,
(b) di-alkylated aromatic species, and
(c) oligomerized olefins species.

REMOVAL OF NON-ALKYLATED SINGLE-RING AROMATIC HYDROCARBON

In the first step of the process of the present invention, at least some of the non-alkylated single-ring aromatic hydrocarbon is removed from the alkylation reaction product. Preferably, substantially all of the non-alkylated single-ring aromatic hydrocarbon is removed.

The removal of non-alkylated single-ring aromatic hydrocarbon can be accomplished by a variety of known techniques including, but not limited to, distillation and nitrogen sparging.

CATALYST

The catalysts of the present invention are solid, acidic catalysts. They can be a molecular sieve or clay. Preferably, the molecular sieve is a natural zeolite or synthetic zeolite. The catalyst is activated prior to use. Preferably, the activated catalyst is used without exposure to atmospheric water, such as by drying the catalyst at a temperature of at least 150° C. under vacuum or flowing inert, dry gas.

Preferably, the acidic catalyst comprises the acid forms of an acid clay, or a crystalline zeolite or other acidic molecular sieve having a pore size of at least 6 angstroms.

Useful zeolites include zeolite Y, beta, SSZ-25, SSZ-26, and SSZ-33. Other possible catalysts include L zeolite, mordenite, boggsite, cloverite, VPI-5, MCM-41, MCM-36, SAPO-8, SAPO-5, MAPO-36, SAPO-40, SAPO-41, MAPSO-46, CoAPO-50, hexagonal faujasite (EMC-2), gmelinite, mazzite (omega zeolite), offretite, ZSM-18, and ZSM-12. These catalysts are discussed in Rosemarie Szostak's *Handbook of Molecular Sieves* (New York, Van Nostrand Reinhold, 1992).

Useful acidic clays may be derived from naturally occurring or synthetic materials. One skilled in the art would realize that there are a number of such clays which are known to be alkylation catalysts. Examples of such acidic clays include montmorillonite, laponite, and saponite. Pillared clays may also be used as catalysts.

REDUCED OLEFIN CONTENT PROCESS CONDITIONS

The second step of the process is carried out at a pressure of about from 0 to 1 bar (preferably atmospheric pressure) and a temperature of about from 100° to 250° C. in the presence of an acidic catalyst.

The process conditions are not restricted to maintaining liquid phase operation. The process can be operated using catalysts in either a batch or fixed bed reactor. In the batch mode, a typical method is to use a stirred autoclave or glass flask which may be heated to the desired reaction temperature. A continuous process is most efficiently carried out in a fixed bed process. Space rates in a fixed bed process can be in the range of about from 0.01 to 10 or more weight hourly space velocity (WHSV).

PRODUCT OF THE REDUCED OLEFIN CONTENT PROCESS

The present invention provides a process for reducing the residual olefin content of the alkylation reaction product. Besides having less residual olefin, the product of that reduced olefin content process will also have increased heavy alkylate content.

While the mechanism of the reduced olefin content process is not completely understood, it is thought that the main reactions are the alkylation of unreacted aromatics with unreacted olefins to form additional mono-alkylates, and, to a lesser degree, the alkylation of mono-alkylates with unreacted olefins to form heavy alkylates, and transalkylation reactions. The choice of catalyst and process conditions will determine the relative amounts of additional mono-alkylates and heavy alkylates formed.

EXAMPLES

The invention will be further illustrated by the following examples, which set forth particularly advantageous method embodiments. While the Examples are provided to illustrate the present invention, they are not intended to limit it.

EXAMPLE 1

A commercial acidic zeolite Y powder having a silica to alumna ratio of about 60:1 was converted into an extrudate (mixture of 80% zeolite and 20% $Al_2O_3$) catalyst by mixing the zeolite Y powder with acid-peptized alumina and extruding, using methods known to those skilled in the art. The resulting extrudate was $\frac{1}{20}$" diameter. The extrudates were calcined. This catalyst was crushed and sieved to produce catalyst particles with a size from 20 to 40 mesh. This powder (0.5 gm) was placed in a metal reactor fitted with a TEFLON insert (Parr Acid Digestion Bomb, Model No. 4749) and the reactor was placed in an oven at 100° C. in air for approximately 19 hours. The reactor was then removed from the oven and immediately closed with the lid.

After the reactor had cooled to room temperature, it was opened and 10.0 gms of an alkylation reaction product ($C_{20-24}$ olefin on toluene, distilled and nitrogen sparged) was quickly added and the reactor was re-closed. The reactor was then placed in an oven at 150° C. After 77 hrs, the reactor was removed from the oven and allowed to cool to room temperature. The contents of the reactor were filtered through filter paper and the catalyst washed with a 1–2 ml of toluene to afford the reduced olefin content process product. Analysis of the alkylation reaction product and the product of the reduced olefin content process by Supercritical Fluid Chromatography (SFC) showed the following results:

| SFC ANALYSIS (WEIGHT %) | | |
| --- | --- | --- |
| | Alkylation Reaction Product | Reduced Olefin Content Process Product |
| Unreacted $C_{20-24}$ Olefin | 2.5 | 1.4 |
| Mono-Alkylate | 94.4 | 87.2 |
| Heavy Alkylate | 3.1 | 11.4 |

While the mechanism of the reduced olefin content process is not completely understood, in this Example it is thought that the transalkylation reaction appears to be prevalent.

EXAMPLE 2

To a 30 cc glass serum bottle was added 0.25 grams of Filtrol F-24 acid clay catalyst granules (available from Englehard Corporation, Elyria, Ohio). The bottle was then placed in an oven at 100° C. in air for approximately 21 hours. The bottle was then removed from the oven and immediately sealed with a TEFLON rubber faced septum using a crimpon tool. After the bottle had cooled to room temperature, 10 grams of an alkylation reaction product ($C_{20-24}$ olefin on toluene, distilled and nitrogen sparged) was added to the bottle via syringe. The bottle was then placed in an oil bath maintained at between 145° C. and 155° C. After 48 hours, the bottle was removed and allowed to cool to room temperature and then the bottle was opened and the contents were gravity filtered through filter paper. Analysis of the alkylation reaction product and the product of the reduced olefin content process by SFC showed the following results:

SFC ANALYSIS (WEIGHT %)

| | Alkylation Reaction Product | Reduced Olefin Content Process Product |
|---|---|---|
| Unreacted $C_{20-24}$ Olefin | 23.8 | 4.9 |
| Mono-Alkylate | 75.4 | 82.1 |
| Heavy Alkylate | 0.8 | 13.0 |

It is felt that the reduced olefin content process product, in this Example, reflects the presence of toluene in the feed.

EXAMPLE 3

The zeolite Y catalyst extrudate used in Example 1 was crushed and sieved to obtain particles with a size between 20 and 40 mesh. The crushed catalyst (2.08 grams) was charged to a ½" OD fixed bed reactor with inert alundum packing above and below the catalyst. The catalyst bed was positioned to be in the isothermal zone of a single zone furnace. The catalyst was activated by flowing over it dry nitrogen gas (100 SCCM) and heating at 180° C. for 21 hours. An alkylation reaction product ($C_{20-24}$ olefin alkylated on toluene, wherein unreacted toluene was reduced by distillation and nitrogen sparging to 0.35 weight % toluene) having 1.1 weight % unreacted $C_{20-24}$ olefin was allowed to flow in an upflow mode through the catalyst bed at a rate of 0.13 grams/minute (2.0 WHSV) vented to atmospheric pressure. The product from the olefin reduction process was collected at various time, weighed and analyzed by SFC for residual olefin content. The following table summarizes the results observed:

| Sample | Time (hrs) | Measured WHSV | Unreacted Olefin (Weight %) | Mono-Alkylate (Weight %) | Heavy Alkylate (Weight %) |
|---|---|---|---|---|---|
| Feed | — | — | 1.07 | 98.21 | 0.73 |
| 1 | 19 | 2.19 | 0.93 | 97.64 | 1.43 |
| 2 | 26.5 | 2.24 | 0.81 | 97.67 | 1.23 |
| 3 | 33.5 | 2.12 | 0.70 | 98.01 | 1.35 |
| 4 | 49.5 | 2.18 | 0.78 | 97.97 | 1.25 |

PROCEDURE FOR DETERMINING RESIDUAL OLEFIN CONTENT OF $C_{20-24}$ ALKYL TOLUENE ALKYLATES BY SUPERCRITICAL FLUID CHROMATOGRAPHY (SFC)

A Dionex, Lee Scientific Model 600 Supercritical Fluid Chromatograph (SFC) equipped with a 10 meter×195 micron OD/50 micron ID, 0.25 micron film (SB-Methyl-100) capillary column, and FID detector operating at 325° C. and carbon dioxide eluent was used with split injection. The following density ramp program was used (isothermal oven at 100° C.):

Initial Density =0.2 g/cc

Inject Sample

Hold five minutes

Ramp to 0.3 g/cc at 0.02 g/cc/min

Ramp to 0.5 g/cc at 0.01 g/cc/min

Ramp to 0.76 g/cc at 0.02 g/cc/min

Hold twelve minutes

For the $C_{20-24}$ Toluene alkylate under the conditions that contribute to the relative retention times (carrier gas flow, condition of the column, and other factors), the $C_{20-24}$ unreacted olefins eluted between 22 and 27.5 minutes. The $C_{20-24}$ toluene mono-alkylate eluted between 28 and 36.5 minutes, and the "heavy alkylate" eluted between 37 and 45 minutes.

Residual olefin content, mono-alkylate content, and "heavies" content were calculated as follows:

$$\text{Percent Residual Olefin} = \frac{\text{Peak Area between 22 and 27.5 minutes}}{\text{Peak Area between 22 and 45 minutes}} \times 100$$

$$\text{Percent Mono-Alkylate} = \frac{\text{Peak Area between 28 and 36.5 minutes}}{\text{Peak Area between 22 and 45 minutes}} \times 100$$

$$\text{Percent Heavy Alkylate} = \frac{\text{Peak Area between 37 and 45 minutes}}{\text{Peak Area between 22 and 45 minutes}} \times 100$$

While the present invention has been described with reference to specific embodiments, this application is intended to cover those various changes and substitutions that may be made by those skilled in the art without departing from the spirit and scope of the appended claims.

What is claimed is:

1. A process for reducing the residual olefin content of the alkylation reaction product of a single-ring aromatic hydrocarbon with an olefin having at least sixteen carbon atoms, said process comprising:

(a) removing at least a portion of non-alkylated single-ring aromatic hydrocarbon from the alkylation reaction product to produce a remainder product having less non-alkylated single-ring aromatic hydrocarbon content; and (b) reacting said remainder product of step (a) at a pressure of about from 0 to 1 bar and at a temperature of about from 100° to 250° C. in the presence of an acidic catalyst selected from the group consisting of molecular sieves and clays, thereby producing a final alkylation reaction product having increased heavy alkylate content and reduced residual olefin content, and wherein said final alkylation reaction product is at least 82 weight % mono-alkylate.

2. A process according to claim 1 wherein the molecular sieve is selected from the group consisting of natural zeolites and synthetic zeolites.

3. A process according to claim 1 wherein the reaction in step (b) is carried out at atmospheric pressure.

4. A process according to claim 1 wherein said single-ring aromatic hydrocarbon is selected from the group consisting of toluene, benzene, xylene, and mixtures thereof.

5. A process according to claim 4 wherein said single-ring aromatic hydrocarbon is toluene.

6. A process according to claim 1 wherein said olefin has from 20 to 28 carbon atoms.

7. An alkylation reaction product of a single-ring aromatic hydrocarbon having a reduced residual olefin content produced by the process according to claim 1.

8. A process for reducing the residual olefin content of the alkylation reaction product of toluene with an olefin having from 20 to 28 carbon atoms, said process comprising:

(a) removing at least a portion of the non-alkylated toluene from the alkylation reaction product to produce a remainder product having less non-alkylated toluene content; and (b) reacting said remainder reacting said remainder product of step (a) at about atmospheric pressure and at a temperature of about from 100° to 250° C. in the presence of an acidic catalyst selected from the group consisting of natural zeolites, synthetic zeolites, and clays, thereby producing a final alkylation reaction product having increased heavy alkylate content and reduced residual olefin content, and wherein said final alkylation reaction product is at least 82 weight % mono-alkylate.

\* \* \* \* \*